(12) United States Patent
Penegor et al.

(10) Patent No.: US 11,116,867 B1
(45) Date of Patent: *Sep. 14, 2021

(54) RESORBABLE EMBOLIZATION SPHERES

(71) Applicant: Teleflex Life Sciences Limited, Valletta (MT)

(72) Inventors: Stephen Penegor, Watertown, MN (US); Jason Isenburg, Victoria, MN (US); James Murto, Maple Grove, MN (US)

(73) Assignee: TELEFLEX LIFE SCIENCES LIMITED, Valletta (MT)

(*) Notice: Subject to any disclaimer, the term of this patent is extended or adjusted under 35 U.S.C. 154(b) by 0 days.

This patent is subject to a terminal disclaimer.

(21) Appl. No.: 16/034,695

(22) Filed: Jul. 13, 2018

Related U.S. Application Data

(60) Continuation of application No. 15/664,358, filed on Jul. 31, 2017, now abandoned, which is a division of application No. 15/131,534, filed on Apr. 18, 2016, now Pat. No. 10,071,181.

(60) Provisional application No. 62/148,889, filed on Apr. 17, 2015.

(51) Int. Cl.
*A61L 24/10* (2006.01)
*A61L 24/00* (2006.01)

(52) U.S. Cl.
CPC ......... *A61L 24/104* (2013.01); *A61L 24/0015* (2013.01); *A61L 24/0042* (2013.01); *A61L 2300/416* (2013.01); *A61L 2400/06* (2013.01); *A61L 2430/36* (2013.01)

(58) Field of Classification Search
None
See application file for complete search history.

(56) References Cited

U.S. PATENT DOCUMENTS

| | | | |
|---|---|---|---|
| 4,028,876 A | 6/1977 | Delatorre | |
| 4,374,063 A | 2/1983 | Consolazio et al. | |
| 4,492,720 A | 1/1985 | Mosier | |
| 5,614,204 A | 3/1997 | Cochrum | |
| 5,635,215 A | 6/1997 | Boschetti et al. | |
| 6,169,071 B1* | 1/2001 | Blaschuk | C07K 7/06 435/7.21 |
| 6,183,497 B1 | 2/2001 | Sing et al. | |
| 6,191,193 B1 | 2/2001 | Lee et al. | |
| 6,676,971 B2 | 1/2004 | Groupil et al. | |
| 6,680,046 B1 | 1/2004 | Boschetti | |
| 7,442,385 B2 | 10/2008 | Lewis et al. | |
| 7,591,993 B2 | 9/2009 | Boschetti | |
| 7,670,592 B2 | 3/2010 | Boschetti | |
| 7,794,755 B2 | 9/2010 | Figuly et al. | |
| 7,838,035 B2 | 11/2010 | Figuly | |
| 7,838,699 B2 | 11/2010 | Schwarz et al. | |
| 8,114,436 B2 | 2/2012 | O'gara et al. | |
| 8,226,926 B2 | 7/2012 | Reb | |
| 8,617,132 B2 | 12/2013 | Golzarian et al. | |
| 8,658,214 B2 | 2/2014 | Rodriguez et al. | |
| 8,697,137 B2 | 4/2014 | Vogel et al. | |
| 8,741,351 B2 | 6/2014 | Vogel et al. | |
| 9,107,850 B2 | 8/2015 | Fritz et al. | |
| 9,114,162 B2 | 8/2015 | Fritz et al. | |
| 2002/0115096 A1* | 8/2002 | Arimori | G01N 33/533 435/6.11 |
| 2002/0187172 A1 | 12/2002 | Reb et al. | |
| 2003/0198595 A1 | 10/2003 | Goldenberg et al. | |
| 2003/0219461 A1 | 11/2003 | Britten et al. | |
| 2004/0068039 A1 | 4/2004 | Lyoo et al. | |
| 2004/0161466 A1 | 8/2004 | Lewis et al. | |
| 2005/0003007 A1 | 1/2005 | Boix et al. | |
| 2006/0057198 A1 | 3/2006 | Lewis et al. | |
| 2006/0177513 A1 | 8/2006 | Martin et al. | |
| 2007/0031467 A1 | 2/2007 | Abrahams et al. | |
| 2007/0208102 A1* | 9/2007 | Reynaud | A61K 6/083 523/115 |
| 2008/0033366 A1 | 2/2008 | Matson et al. | |

(Continued)

OTHER PUBLICATIONS

Vandelli et al., Gelatin microspheres crosslinked with D,L-glyceraldehyde as a potential drug delivery system: preparation, characterisation, in vitro and in vivo studies, International Journal of Pharmaceutics 215 (2001) 175-184 (Year: 2015).*

Fu et al., Evaluation of BSA protein release from hollow hydroxyapatite microspheres into PEG hydrogel, Materials Science and Engineering C 33 (2013) 2245-2250 (Year: 2013).*

Young etal., Gelatin as a delivery vehicle for the controlled release of bioactive molecules, Journal of Controlled Release 109 (2005) 256-274 (Year: 2005).*

Wei et al., Gelatin microspheres encapsulated with a nonpeptide angiogenic agent, ginsenoside Rg1, for intramyocardial injection in a rat model with infarcted myocardium, Journal of Controlled Release 120 (2007) 27-34) (Year: 2007).*

(Continued)

*Primary Examiner* — Jennifer A Berrios
(74) *Attorney, Agent, or Firm* — Dorsey & Whitney LLP

(57) ABSTRACT

Embolic materials, suspensions, kits and related methods useful for embolization are disclosed. An embolic material can comprise a resorbable microsphere including cross-linked gelatin as its primary ingredient and having a substantially spherical shape with a diameter of about 50 micrometers to about 1,500 micrometers, inclusive. The microsphere can optionally include one or both of a marker or an active agent. The microsphere can be cross-linked, such as with glutaraldehyde or formaldehyde, which can affect the microsphere's in vivo degradation profile and ability to withstand a sterilization process at certain temperatures. In an embodiment, the microspheres can resorb during an in vivo time period of between about 24 hours and about 15 weeks, inclusive. An embolization suspension can include a plurality of resorbable microspheres and a liquid carrier, and the suspension can be disposed in a syringe, vial or other applicator for administration to a patient.

14 Claims, 6 Drawing Sheets

(56) References Cited

U.S. PATENT DOCUMENTS

| | | | |
|---|---|---|---|
| 2008/0220077 A1* | 9/2008 | Vogel | A61K 9/1635 424/489 |
| 2009/0131303 A1 | 5/2009 | Hong et al. | |
| 2010/0021550 A1 | 1/2010 | Li et al. | |
| 2011/0104052 A1 | 5/2011 | Barnett et al. | |
| 2011/0182998 A1 | 7/2011 | Reb et al. | |
| 2012/0123355 A1 | 5/2012 | Delap et al. | |
| 2013/0252900 A1 | 9/2013 | Reb et al. | |
| 2014/0030350 A1 | 1/2014 | Ashrafi et al. | |
| 2014/0271757 A1* | 9/2014 | Agrawal | A01N 25/22 424/405 |
| 2014/0274945 A1 | 9/2014 | Blaskovich et al. | |
| 2015/0018800 A1 | 1/2015 | Reb et al. | |
| 2015/0328361 A1 | 11/2015 | Delap et al. | |

OTHER PUBLICATIONS

Akin et al., "Preparation and Characterization of Crosslinked Gelatin Microspheres," Journal of Applied Polymer Science, 1995, pp. 95-100, vol. 58.

Elzoghby, "Gelatin-based Nanoparticles as Drug and Gene Delivery Systems: Reviewing Three Decades of Research," Journal of Controlled Release, 2013, pp. 1075-1091, vol. 172.

Fu et al., "Evaluation of BSA Protein Release From Hollow Hydroxyapatite Microspheres Into PEG Hydrogel," Materials Science and Engineering, 2013, pp. 2245-2250, vol. 33.

Islam et al., "Physico-Chemical Characteristics of Gamma-Irradiated Gelatin," Prog. Biomater., 2014, pp. 1-9, vol. 3, No. 21.

Lu et al., "Lung-Targeting Microspheres of Carboplatin," International Journal of Pharmaceutics, 2003, pp. 1-11, vol. 265.

Mastro, "Irradiation of Gelatin. Important Applications for the Development of New Materials," Memorias en CDROM, 2011, pp. 1-6.

Santoro et al., "Gelatin Carriers for Drug and Cell Delivery in Tissue Engineering," Journal of Controlled Release, 2014, pp. 210-218, vol. 190.

Truong-Le et al., "Controlled Gene Delivery by DNA-Gelatin Nanospheres," Human Gene Therapy, Aug. 10, 1998, pp. 1709-1717, vol. 9.

Vandelli et al., "Gelatin Microspheres Crosslinked with D,L-glyceraldehyde as a Potential Drug Delivery System: Preparation, Characterisation, in Vitro and In Vivo Studies," International Journal of Pharmaceutics, 2001, pp. 175-184, vol. 215.

Wolanske et al., "Uterine Artery Embolization: Where Does It Stand in the Management of Uterine Leiomyomas? Part 2," Applied Radiology, Oct. 2004, pp. 18-25.

* cited by examiner

RESORBABLE EMBOLIZATION SPHERES

CROSS-REFERENCE TO RELATED APPLICATIONS

This application is a continuation of U.S. patent application Ser. No. 15/664,358, which is a divisional of U.S. patent application Ser. No. 15/131,534 filed Apr. 18, 2016, no U.S. Pat. No. 10,071,181, which claims the benefit of priority under 35 U.S.C. § 119(e) to U.S. Provisional Patent Application Ser. No. 62/148,889, entitled "RESORBABLE EMBOLIZATION SPHERES" filed Apr. 17, 2015, each of which is herein incorporated by reference in its entirety and for all purposes.

TECHNICAL FIELD

This patent document relates to medical devices. More particularly, but not by way of limitation, the patent document relates to embolization.

BACKGROUND

Embolization is the selective blockage of one or more blood vessels supplying a diseased vascular structure or diseased tissue while simultaneously preserving the blood supply to surrounding "normal" vascular structure or tissue. For example, uterine fibroid embolization (UFE) is the process of occluding the vascular blood supply to uterine fibroids to reduce fibroid size and alleviate associated symptoms, including bleeding, pain and disfigurement. Embolization involves the injection and selective placement of embolic material into one or more vessels.

Embolization can be used in a variety of vessels and organs whether healthy or diseased; however, it is more commonly used for conditions such as tumors, vascular malformations and hemorrhagic processes. In the case of tumors, embolization can suppress pain, limit blood loss during surgical intervention following embolization, or bring on tumoral necrosis and avoid the necessity for surgical intervention. In the case of vascular malformations, embolization can enable the blood flow to normal tissues to be normalized, aid in surgery and limit the risk of hemorrhage. In hemorrhagic events or processes, vascular occlusion can produce a reduction of blood flow, which can promote cicatrization of the arterial opening(s).

OVERVIEW

The present inventors recognize that resorbable microspheres including cross-linked gelatin as their primary ingredient can provide a safe and effective embolization treatment. The resorbable nature of the microspheres is believed to be desirable to many patients, particularly younger patients, who do not want permanent materials implanted within their body. The spherical shape and calibrated size ranges of the microspheres offer smooth delivery and predictable distribution within a vessel or other lumen. In addition, spherical particles can penetrate to a target region within vasculature more easily than traditional irregularly-shaped particles due to their uniform shape. The present inventors further recognize that there are numerous clinical situations, for example, trauma, postpartum hemorrhage and gastrointestinal tract (GI) bleeding, in which temporary embolization may be desirable; however, the majority of embolic materials used today embolize permanently. Temporary embolization can allow for the temporary blockage of blood flow to a punctured or diseased site, allowing the blood vessel or site to heal. As the temporary resorbable microspheres degrade, the blood vessel can recanalize reestablishing the original vasculature.

The present inventors have intensively investigated embolic materials in the form of resorbable microspheres including cross-linked gelatin as their primary ingredient, as well as methods for producing such embolic materials. An example embolic material can comprise a resorbable microsphere including cross-linked gelatin and having a substantially spherical shape with a diameter of about 50 micrometers to about 1,500 micrometers, inclusive. The microsphere can optionally include one or both of a marker or an active agent. The microsphere can be cross-linked, such as with glutaraldehyde or formaldehyde, which can affect the microsphere's in vivo degradation profile and ability to withstand a sterilization process at certain temperatures. In an embodiment, the microspheres can resorb during an in vivo time period of between about 24 hours and about 15 weeks, inclusive. An embolization suspension can include a plurality of resorbable microspheres and optionally a liquid carrier and it can be disposed in a syringe, vial or other applicator for administration to a patient.

An example method of forming an embolic material can comprise preparing a gelatin solution by combining water and at least 12% irradiated gelatin, such as between about 12% and about 22% of gelatin; sonicating the gelatin solution to remove air; introducing the gelatin solution into heated oil to form a mixture of gelatin solution and oil; agitating the mixture to form a plurality of resorbable microspheres having a substantially spherical shape with a diameter ranging from about 50 micrometers to about 1,500 micrometers, inclusive; and cross-linking the plurality of resorbable microspheres.

These and other examples and features of the present teachings will be set forth, at least in part, in the following Detailed Description. This Overview is intended to provide non-limiting examples of the present teachings—it is not intended to provide an exclusive or exhaustive explanation. The Detailed Description below is included to provide further information about the present embolic materials and related suspensions, kits and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in this patent document.

Figure 1:
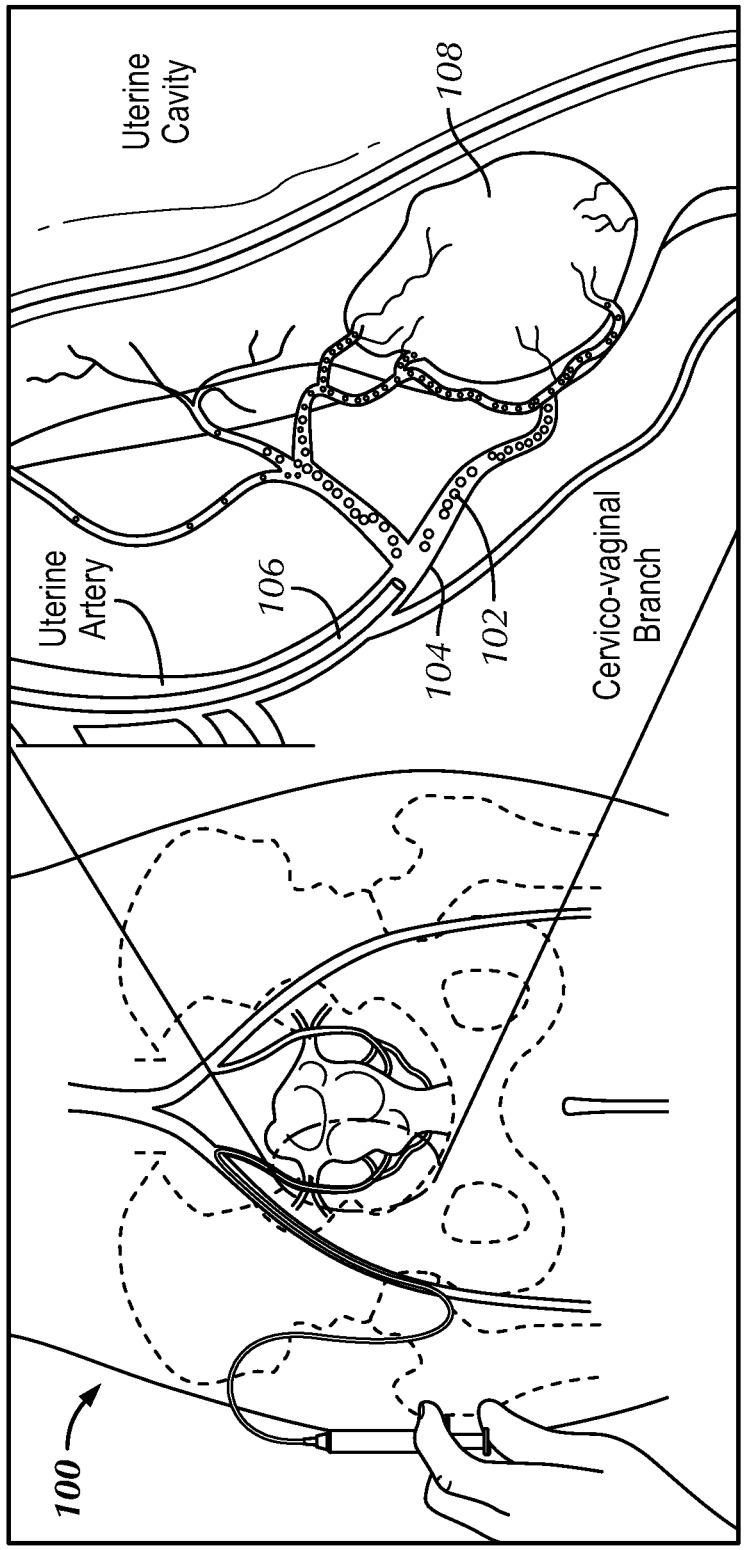
FIG. 1 illustrates an example embolization application, particularly uterine fibroid embolization.

The drawing figures are not necessarily to scale. Certain features and components may be shown exaggerated in scale or in schematic form, and some details may not be shown in the interest of clarity and conciseness.

DETAILED DESCRIPTION

Definitions

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "(bio)absorbable," "(bio)degradable," and "(bio)resorbable" refer to the ability of a material to disintegrate or degrade so that no material remains after a predetermined period of time, such as after 24 hours, after 15 weeks, or any period of time therebetween.

The term "microsphere(s)" refers to an absorbable, degradable or resorbable particle which may be suspended in biological or biologically-compatible liquids, and which have, under microscopic examination, a substantially spherical shape. When viewing any cross-section of the microsphere, the difference between the average major diameter and the average minor diameter is less than about 20%.

The term "lumen" refers to various hollow organs or vessels of the body, such as veins, arteries, intestines, fallopian tubes, trachea, and the like.

The term "embolic material" refers to a composition or agent introduced into a lumen that partially or totally fills or plugs the space or cavity. For example, an embolic material can be used for occlusion of a vessel leading to a tumor or fibroid, occlusion of a vascular malformation, such as an arteriovenous malformation (AVM), occlusion of a left atrial appendage, as a filler for an aneurysm sac, as an endoleak sealant, as an arterial sealant, as a puncture sealant, or for occlusion of any other lumen such as, for example, a fallopian tube.

The term "effective amount" refers to an amount of microspheres sufficient to temporarily occlude a target lumen or that is sufficient to result in amelioration of symptoms or a prolongation of survival in a patient.

The terms "treat," "treatment" and "treating" refer to the reduction or amelioration of the progression, severity or duration of a given disease resulting from the administration of one or more therapies (including, but not limited to, the administration of microspheres of the present teachings). In certain embodiments, the terms refer to the reduction of pain associated with one or more diseases or conditions.

The terms "administer" and "administration" refer to the act of injecting or otherwise physically delivering a microsphere into a patient, such as through the use of a delivery catheter.

The term "active agent" refers to any substance that provides therapeutic effects to the process of angiogenesis-dependent diseases or biological or physiological responses to the angiogenesis-dependent diseases. An example of a therapeutic agent is an anti-inflammation agent that prevents or reduces the effect of inflammations associated with angiogenesis-dependent diseases.

The term "sonication" refers to the act of applying sound energy (e.g., ultrasonication) to agitate particles in a sample (e.g., a gelatin solution) for degassing purposes.

The terms "distal" and "proximal" refer to a position or direction relative to a treating clinician. "Distal" and "distally" refer to a position that is distant, or in a direction away, from the clinician. "Proximal" and "proximally" refer to a position that is closer to, or in a direction toward, the clinician.

The terms "patient" and "subject" refer to a mammal such as a non-primate (e.g., cows, pigs, horses, cats, dogs, rats, etc.) or a primate (e.g., monkey and human), most preferably a human. In some embodiments, the subject is an infant, child, adult or elderly subject.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Example Applications of the Present Teachings

As illustrated in FIG. 1, embolization 100 is a non-surgical, minimally-invasive procedure in which an embolic material 102 is injected into a target lumen 104 to at least partially fill or plug the space or cavity and/or encourage clot formation so that blood flow through the lumen is reduced or stopped. A delivery catheter 106 can be placed into the lumen 104 and an appropriate size embolic material 102 can be introduced to create an occlusion. Recognized advantages of embolization 100 over open surgical procedures include faster recovery time, lower risk of infection, minimally invasive, and less use of anesthesia.

Embolization 100 can be used to treat a wide variety of conditions that affect different organs in the body and can be performed anywhere in the body that a delivery catheter 106 can be placed. Embolization 100 may be used in treating skin, head or neck tumors, tumors of the uterus or fallopian tubes, liver or kidney tumors, endometriosis, fibroids, etc. Particularly, embolization 100 has been used for AVM of the pelvis, kidney, liver, spine and brain. Uterine artery embolization has been used for the treatment of fibroids 108; renal artery embolization has been used for the treatment of renal angiomyolipomas and renal cell carcinoma; intracranial embolization has been used for the treatment of cerebral and intracranial aneurysms, neuroendocrine metastases, intracranial dural arteriovenous fistula and patent ductus arteriosus. Other examples of specific embolization procedures include hepatic artery embolization and pulmonary artery embolization. Each of the above diseases or disorders, among others, is within the scope of the present teachings.

The vast majority of embolic materials embolize permanently; however, there are numerous clinical situations in which temporary embolization or temporary materials are desired. Temporary embolization may be desired, for example, in treatment of tumors to allow for recanalization and reapplication of a chemotherapeutic agent to the tumor. As another example, temporary occlusion may be desirable when using the embolic composition for temporary sterilization. Temporary occlusion can be achieved by using a fully or partially resorbable embolic material. Temporary materials are desired by patients who prefer not to have a permanent foreign material implanted in their body.

The temporary embolic material used most frequently today in the clinical setting is Gelfoam® compressed sponge (Pfizer Inc., New York, N.Y.). This embolic material comes in the form of foam sheets. Physicians cut sheet Gelfoam into irregularly-shaped pieces and inject them through a lumen of a delivery catheter. Disadvantages of these pieces can include their non-precise size and open edges on the pieces that can cause them to clump together and subsequently plug up the delivery catheter. Additionally, it is difficult to properly and completely occlude a lumen using irregularly-shaped particles, because they cannot establish complete contact with all lumen surfaces, which are typically cylindrical. Gelfoam is degraded by proteases in the blood stream. However, due to differences in enzyme expression from one patient to another and variation in the size of the pieces of Gelfoam used, the in vivo degradation times of this embolic material can span an unpredictable, oftentimes too short, timeframe.

Figure 2:
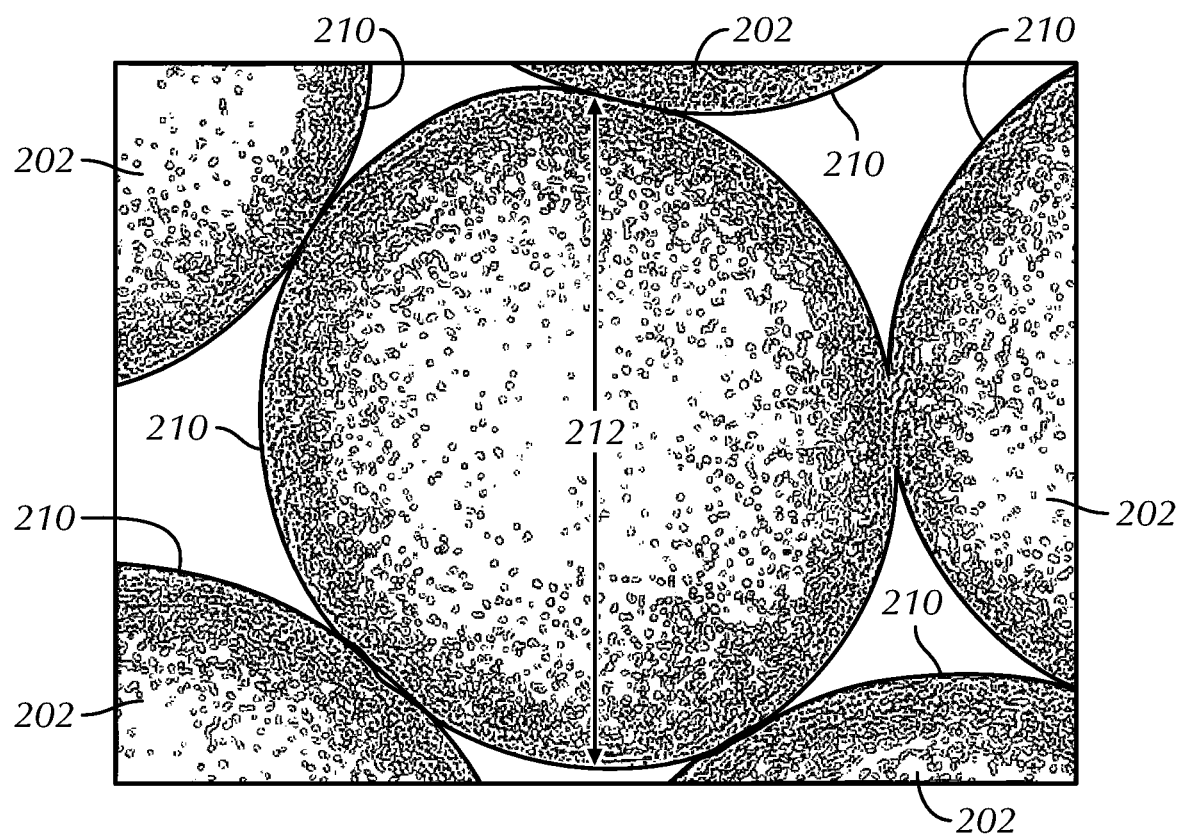
FIG. 2 illustrates a magnified view of a plurality of embolic materials in the form of resorbable microspheres, as constructed in accordance with at least one embodiment.

Resorbable Microspheres Including Cross-Linked Gelatin:

The present teachings provide embolic materials in the form of resorbable microspheres 202, as shown in FIG. 2. The microspheres 202 have cross-linked gelatin as their primary ingredient. In an example, the microspheres 202 can be made from porcine gelatin (e.g., purified porcine skin gelatin) through an emulsion system, and subsequently crosslinked. Gelatin contains chains of amino acids, including RGD peptides (arginine-glycine-aspartic acid sequences). RGD peptides can modulate cell adhesion, and can ultimately improve biological performance and biocompatibility of gelatin material in comparison to synthetic polymers, which lack these cell recognition sequences. Difunctional chemical agents reacting on the gelatin aminos, which can be effective cross-linkers, include glutaraldehyde, formaldehyde, glyoxal, and the like. Cross-linking gelatin with glutaraldehyde, for example, can form stable bonds between certain amino acids and can increase the gelatin's resistance to degradation in vivo. Because the gelatin is cross-linked, it can withstand sterilization and provide controlled degradation once implanted such that it is absorbed more slowly than Gelfoam. Cross-linking can also improve the mechanical strength of the gelatin microspheres 202 allowing for fracture-free delivery into a lumen of a patient.

The resorbable microspheres 202 have a substantially spherical shape with a smooth outer surface 210 and can be manufactured to be within calibrated size ranges. In varying examples, the microspheres 202 can have a diameter 212 ranging from about 50 micrometers (µm) to about 1,500 µm and can be available in size ranges such as 100-300 µm, 300-500 µm, 500-700 µm or 700-1,000 µm. The size range selected can vary with the nature, type, location and severity of the condition to be treated and/or the route of administration. It can also vary with age, weight and the response of the patient. An effective amount of microspheres 202 for a particular treatment can range between a few hundred to many thousand particles, but may alternatively be more or less.

Advantages of the microspheres 202 and their spherical shape are numerous. For example, the microspheres 202 can provide proper and complete occlusion of a lumen because they can establish near complete contact with all surfaces of a lumen to be occluded. Additionally, samples or suspensions containing the microspheres 202 will not block or clog delivery catheters, because they always have the same or nearly the same dimension regardless of their space orientation in the delivery catheter. Moreover, due to their smooth outer surface 210, little or no attrition will occur and small-sized particles will not be generated from the microspheres, thereby avoiding potentially fatal complications, such as pulmonary embolization. Furthermore, the microspheres 202 can interact with each other at a single point and such contact is typically not enough to induce aggregation by surface interaction.

The microspheres 202 or a carrier in which the microspheres are suspended or delivered can optionally include a marker, making detection of the microspheres within a patient possible. The marker can be employed as a component of the microspheres 202, coated onto a surface of the microspheres, or administered as part of the carrier with the microspheres, as further discussed below. The marker can be any material (e.g., dye, an imaging agent or a contrast agent) capable of enhancing contrast in a desired imaging modality (e.g., magnetic resonance, X-ray (e.g., CT), ultrasound, magnetotomography, electrical impedance imaging, light imaging (e.g. confocal microscopy and fluorescence imaging) or nuclear imaging (e.g. scintigraphy, SPECT and PET)). The marker can be water soluble or water insoluble. Examples of water soluble markers include metrizamide, iopamidol, iothalamate sodium, iodomide sodium and meglumine. Examples of water insoluble markers include tantalum, tantalum oxide, barium sulfate, gold, tungsten and platinum. The amount of marker included in a microsphere 202 should be sufficient to allow its detection.

The microspheres 202 can also optionally include an active agent that provides for the synergistic treatment of a condition and its symptoms. Release of the incorporated additive from the microspheres 202 can be achieved by diffusion of the agent from the microspheres, degradation of the microspheres, and/or degradation of a chemical link coupling the agent to the gelatin. Active agents that may be desirable to deliver with the microspheres include prophylactic, therapeutic, and diagnostic agents including organic and inorganic molecules and cells.

Examples of active agents that can be incorporated include, but are not limited to, chemotherapeutic agents, anti-angiogenic agents, cells, circulatory drugs, anti-tubercular agents, anti-viral agents, anti-anginal agents, antibiotics, anti-inflammatory agents, anti-protozoan agents, anti-rheumatic agents, narcotics, cardiac glycoside agents, neuromuscular blocking agents, sedatives, local anesthetic agents, general anesthetic agents and radioactive particles. Chemotherapeutic agents that can be incorporated include water soluble chemotherapeutic agents, such as cisplatin (platinol), doxorubicin (adriamycin, rubex), gemcitabine (gemzar), irinotecan (camptosar) or mitomycin C (mutamycin). Other chemotherapeutic agents include iodinated fatty acid ethyl esters of poppy seed oil, such as lipiodol. Cells that can be incorporated into the embolic compositions include cells to encourage tissue growth or cells to secrete a desired active agent. For example, cells that can be incorporated include fibroblasts, endothelial cells, muscle cells, stem cells, etc. Cells can be modified to secrete active agents such as growth factors. Circulatory drugs include, for example, propranolol. Anti-tubercular agents include, for example, para-aminosalicylic acid, isoniazid, capreomycin sulfate cycloserine, ethambutol hydrochloride ethionamide, pyrazinamide, rifampin, and streptomycin sulfate. Anti-viral agents include, for example, acyclovir, amantadine azidothymidine (AZT or Zidovudine), ribavirin, and vidarabine monohydrate (adenine arabinoside, ara-A). Anti-anginal agents include, for example, diltiazem, nifedipine, verapamil, erythritol tetranitrate, isosorbide dinitrate, nitroglycerin (glyceryl trinitrate), and pentaerythritol tetranitrate. Antibiotics include, for example, dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, and tetracycline. Anti-inflammatory agents and analgesics include, for example, diflunisal, ibuprofen, indomethacin, meclofenamate, mefenamic acid, naproxen, oxyphenbutazone, phenylbutazone, piroxicam, sulindac, tolmetin, aspirin and salicylates. Anti-protozoan agents include, for example, chloroquine, metronidazole, hydroxychloroquine, quinine, and meglumine antimonate. Anti-rheumatic agents include, for example, penicillamine. Narcotics include, for example, paregoric and opiates, such as codeine, heroin, methadone, morphine and opium. Cardiac glycoside agents include, for example, deslanoside, digitoxin, digoxin, digitalin and digitalis. Neuromuscular blocking agents include, for example, atracurium mesylate, gallamine triethiodide, hexafluorenium bromide, metocurine iodide, pancuronium bromide, succinylcholine chloride (suxamethonium chloride), tubocurarine chloride, and vecuronium bromide. Sedatives (hypnotics) include, for example, amobarbital, amobarbital sodium, aprobarbital, butabarbital sodium, chloral hydrate, ethchlorvynol, ethinam ate, flurazepam hydrochloride, glutethimide, methotrimeprazine hydrochloride, methyprylon, midazolam hydrochloride paraldehyde, pentobarbital, pentobarbital sodium, phenobarbital sodium, secobarbital sodium, talbutal, temazepam, and triazolam. Local anesthetic agents include, for example, bupivacaine hydrochloride, chloroprocaine hydrochloride, etidocaine hydrochloride, lidocaine hydrochloride, mepivacaine hydrochloride, procaine hydrochloride, and tetracaine hydrochloride. General anesthetic agents include, for example, droperidol, etomidate, fentanyl citrate with droperidol, ketamine hydrochloride, methohexital sodium, and thiopental sodium. Radioactive particles or radioactive ions include, for example, strontium, rhenium, yttrium, technetium, and cobalt.

Figure 3:
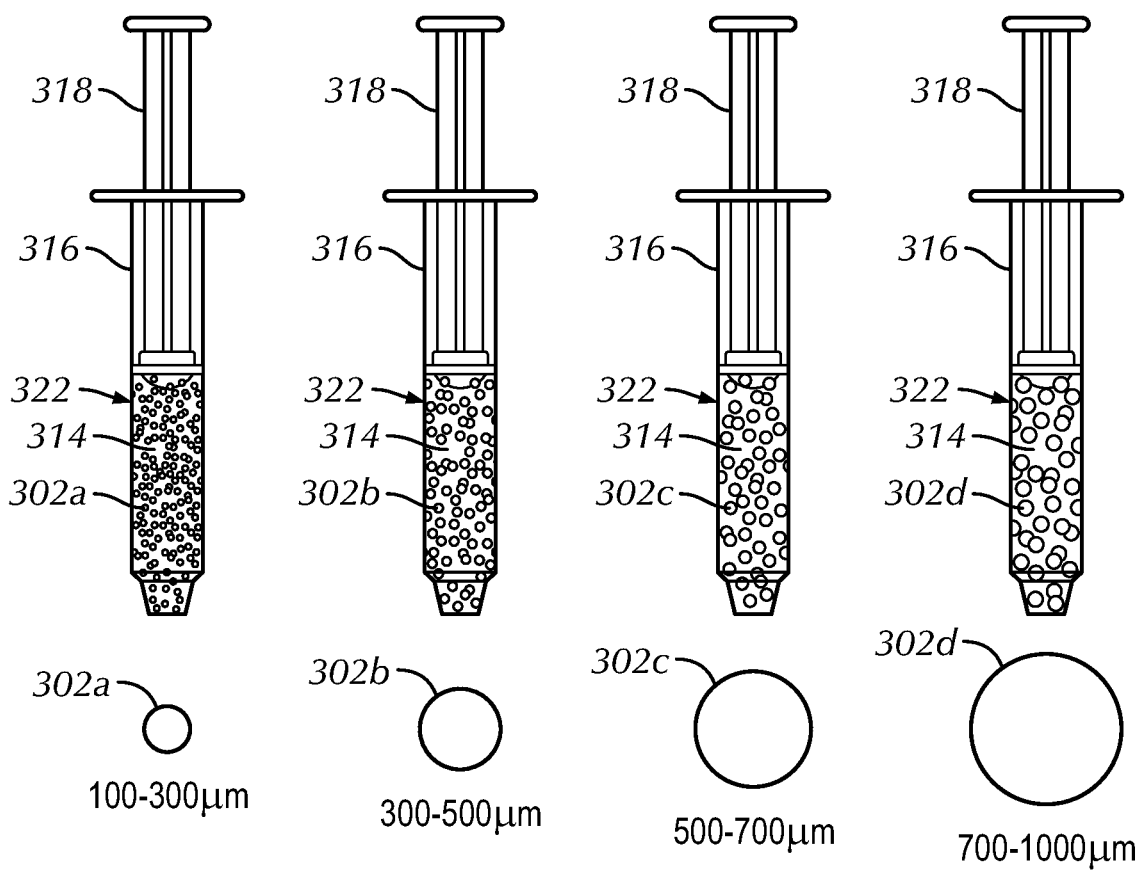
FIG. 3 illustrates injectable suspensions, each suspension including resorbable microspheres of a calibrated size range and a suitable liquid carrier contained within a syringe, as constructed in accordance with at least certain embodiments.

Injectable Suspensions:

FIG. 3 illustrates injectable suspensions 322 suitable for embolization, each of which can comprise resorbable microspheres (including cross-linked gelatin) 302a, 302b, 302c, 302d of varying sizes (e.g., diameter of 100-300 µm, 300-500 µm, 500-700 µm or 700-1,000 µm) and a suitable liquid carrier 314. The liquid carrier 314 allows the microspheres 302a, 302b, 302c, 302d to be stored in suspension and injected as a fluid. More specifically, the hydrophilic nature of the microspheres 302a, 302b, 302c, 302d permits placing them in suspension, and in particular, in the form of sterile injectable suspensions 322, while avoiding the formation of aggregates or adhesion to the walls of storage containers and implantation devices, such as delivery catheters, syringes 316, needles, and the like. In an example, the microspheres 302a, 302b, 302c, 302d and the liquid carrier 314 can be packaged in a 20 milliliter (mL) syringe containing about 1 mL of microspheres suspended in 5 mL of liquid carrier. The size of microspheres 302a, 302b, 302c, 302d included in the syringe 316 can be represented and conveyed to a treating physician by a different colored syringe plunger 318.

The carrier 314 can be any biocompatible fluid capable of delivering the microspheres 302a, 302b, 302c, 302d to a desired site. Examples of suitable materials for the carrier 314 can include saline, dextran, glycerol, polyethylene glycol, corn oil or safflower, or other polysaccharides or biocompatible organic polymers either singly or in combination. When deposited into the blood stream, the carrier 314 can be dispersed or destroyed.

Figure 4:
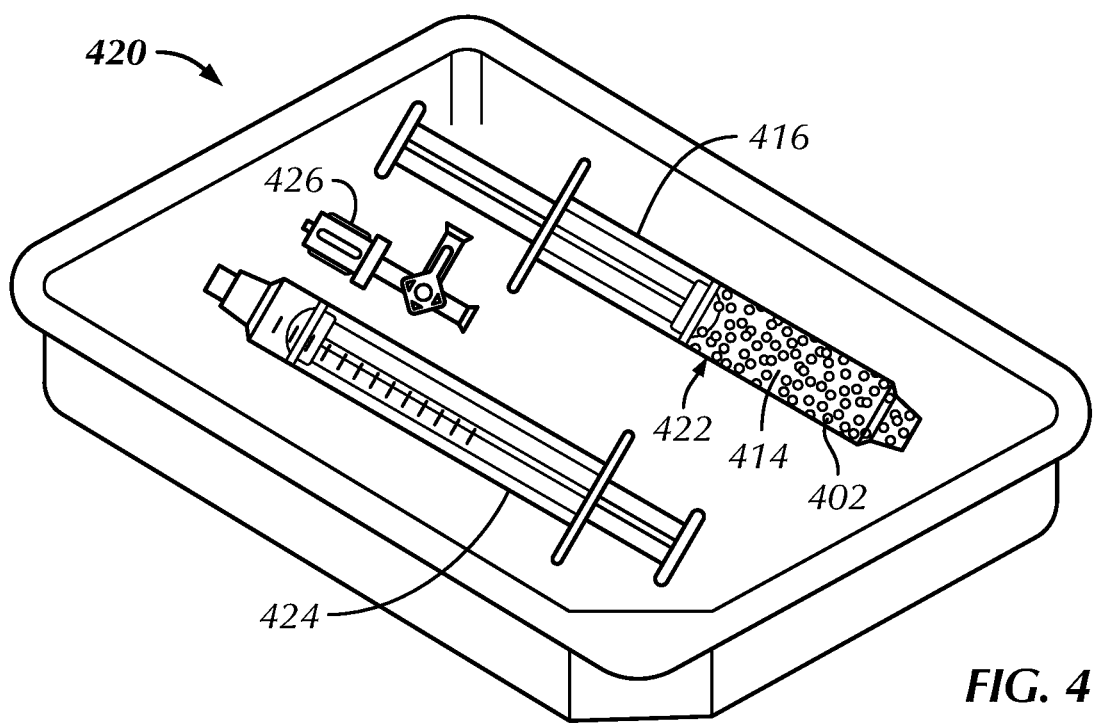
FIG. 4 illustrates a perspective view of a kit including an injectable suspension contained within a syringe and a delivery system, as constructed in accordance with at least one embodiment.
Figure 5:
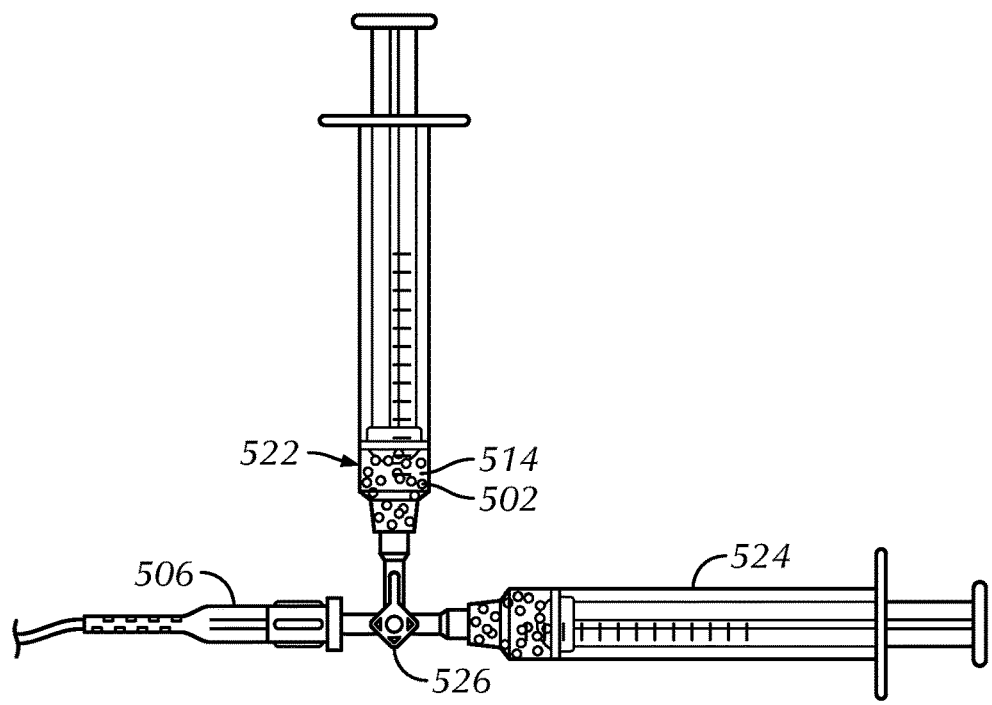
FIG. 5 illustrates an assembled view of the kit of FIG. 4 attached to the proximal end of a delivery catheter, as constructed in accordance with at least one embodiment.

Kits:

FIG. 4 illustrates a kit 420 including a pre-loaded syringe 416 of an injectable suspension 422 and a delivery system (e.g., a mixing or injection syringe 424 and a connection component 426, such as a 3-way stopcock), and optionally one of more of a delivery catheter, a guidewire, a marker (e.g., in the form of contrast agent), and an active agent. The injectable suspension 422 is designed to be delivered through an inner diameter of the delivery catheter and into a lumen, such as an artery, of a patient. The guidewire can be used to position the delivery catheter within the lumen. Instructions, either as inserts or labels, indicating quantities of resorbable microspheres 402 and liquid carrier 414, guidelines for mixing these components, or protocols for administration can also be included in the kit 420. Sterilization of the containers, components, and any materials included in the kit 420 can be carried out using conventional sterilization methodologies known to those skilled in the art.

Alternative kit formats can vary from what is shown in FIG. 4. In one kit format, the resorbable microspheres can be present in a liquid, physiologically compatible carrier in one syringe and contrast and active agents can be provided in a second and/or optionally a third syringe. In certain kit formats, microspheres comprising the contrast agent can be present in one syringe, and active agent can be present in solution in another syringe. In this format, the contents of the two syringes can be mixed together prior to, or concurrently with, administration. In other kit formats, the microspheres, optionally comprising contrast agent and active agent, can be provided in dry form in a syringe or vial (e.g., a vacuum-sealed vial). The dry material can then be suspended in a suitable liquid carrier prior to administration or a second syringe, which contains the injectable solution, can be provided and the contents of both syringes can be combined prior to, or concurrently with, administration. Finally, in another kit format, the microspheres can be present in one syringe and a second syringe can contain a pharmaceutically acceptable solution comprising contrast agent. The microspheres in the first syringe can be pre-loaded with an active agent, or the active agent can optionally be present in a third syringe. The microspheres can then be mixed together with the active agent and/or contrast agent prior to, or concurrently with, administration.

Methods of Use:

The present teachings further relate to a method for embolization, which includes administering to a patient an injectable suspension 522 containing resorbable microspheres 502 and a suitable liquid carrier 514. The microspheres 502 can be implanted to various locations of a patient's body using a delivery system (e.g., a mixing or injection syringe 524 and a connection component 526, such as a 3-way stopcock) and a delivery catheter 506. For example, the compositions can be delivered endovascularly to plug the feeder vessel(s) of a tumor or a uterine fibroid. Any other suitable route of administration (e.g., parenteral, subcutaneous, or intramuscular) can alternatively be employed for providing the patient with an effective dosage of resorbable microspheres at the desired target or location.

Using the assembled delivery system shown in FIG. 6, which can include an injection syringe 624 and a luer-lock 3-way stopcock 626, resorbable microspheres 602 suspended in a liquid carrier 614 can be urged from a pre-loaded syringe 616, received by the injection syringe 624, urged through a delivery catheter 606, and positioned in a target region 628 of a lumen (e.g., blood vessel) 604 in the following manner.

First, access to the lumen 604 can be gained and the delivery catheter 606 can be introduced into the lumen. A hollow needle can be used to pierce the patient's skin and enter bodily tissue at an angle. A guidewire can then be inserted into the hollow needle and advanced percutaneously into the tissue to the target region for delivery of the resorbable microspheres 602. The hollow needle can then be pulled in a backward direction to be removed from the bodily tissue and from contact with the guidewire. Next, the delivery catheter 606 can be advanced along the guidewire to the target region 628. The delivery catheter 606 has a distal end through which the microspheres 602 can be delivered into the target region 628. Generally, the delivery catheter 606 also has a proximal end and a plastic adaptor to receive the microspheres 602. The diameter of the delivery catheter 606 can be based upon the size of the body tissue into which it is inserted. The inner diameter of the delivery catheter 606 can be larger than the diameter of the microspheres 602 to allow their delivery to the target region 628. For example, microspheres 602 having a size range of 100-300 µm or 300-500 µm can be delivered through a delivery catheter 606 having an inner diameter of 0.020 in (0.51 mm), microspheres 602 having a size range of 500-700 µm can be delivered through a delivery catheter 606 having an inner diameter of 0.023 in (0.58 mm), and microspheres 602 having a size range of 700-1,000 µm can be delivered through a delivery catheter 606 having an inner diameter of 0.038 in (0.97 mm). Optionally, an introducer sheath can be used to assist the percutaneous introduction of the delivery catheter 606 into the tissue. The introducer sheath can provide stability to the delivery catheter 606 as it is advanced through the introducer sheath to the target region 628 of the lumen 604.

The 3-way stopcock 626 can be attached to the proximal end or hub of the delivery catheter 606, and the injection syringe 624 can be connected to a first port of the stopcock. In an example, the injection syringe 624 is initially an empty 1 mL syringe that is attached to a female port of the stopcock 626.

The volume of the microspheres 602 and liquid carrier 614 initially in the pre-loaded syringe 616 can be matched with an approximately equivalent volume of undiluted contrast agent (not shown), which can result in a 50% contrast and 50% saline/microsphere solution. The pre-loaded syringe 616, now also including contrast agent, can be connected to a second port of the stopcock 626. In an example, the pre-loaded syringe 616 is a 20 mL syringe. The microspheres 602 can optionally be administered already loaded with an active agent. In other embodiments, the microspheres 602 can be administered in combination with an active agent solution, such as wherein the active agent is administered prior, simultaneously or after the administration of the microspheres.

After ensuring the stopcock 626 port connected to the delivery catheter 606 is closed, an amount of the 50% contrast and 50% saline/microsphere solution can be drawn into the 1 mL injection syringe 624, for example. Any amount of solution ranging up to about 1 mL can be transferred to the injection syringe 624 in this example. The stopcock 626 can then be adjusted such that the injection syringe 624 is only in fluid communication with the lumen of the delivery catheter 606. With the injection syringe 606 in fluid communication with the delivery catheter lumen, a user can inject the small amount of solution from the injection syringe into the delivery catheter 606, thereby loading the microspheres into the delivery catheter lumen under fluoroscopy. The microspheres 602 can then be guided through the delivery catheter 606 and distally beyond the distal end of the delivery catheter to the location within the vascular tissue near or at the target region 628. According to one embodiment, the user depresses the plunger 618 of the injection syringe 624, thereby urging the microspheres 602 into the lumen 604. According to another embodiment, the step of transferring a small amount of solution to the injection syringe 624 and then injecting the small amount into the delivery catheter 606, thereby loading the microspheres, can be repeated once or twice to insure loading of the microspheres 602.

Figure 6:
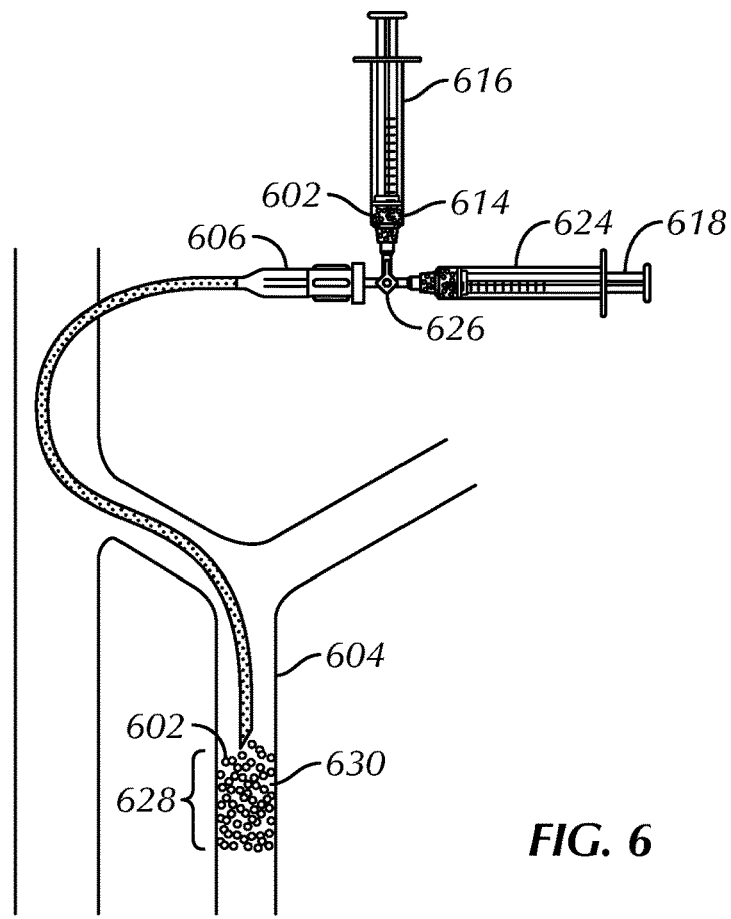
FIG. 6 illustrates the delivery of resorbable microspheres of a calibrated size range into a vessel to create an occlusion of the vascular blood supply, as constructed in accordance with at least one embodiment.
Figure 7:
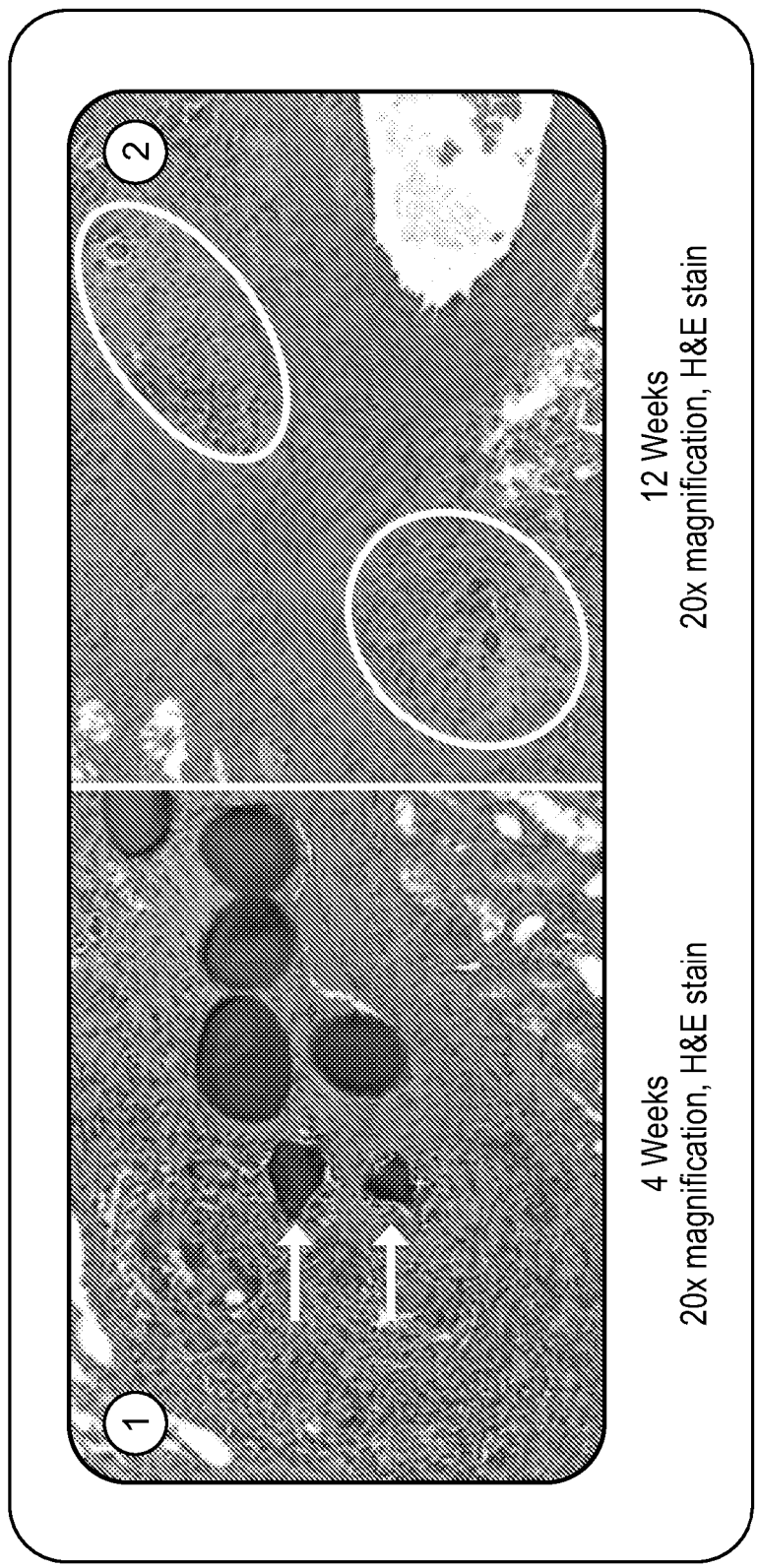
FIG. 7 illustrates degradation of resorbable microspheres at 4 weeks and 12 weeks, as identified from an animal study.

The occlusion of the lumen 604 can be continued until occlusion occurs distally of the bleeding site 630, as shown in FIG. 6, by gentle pulling out the delivery catheter 606 so that the microspheres 602 occlude the lumen by plugging it in a distal-to-proximal direction across the bleeding site. Upon completion of the embolization procedure, the delivery catheter 606 can be removed while maintaining gentle suction so that the microspheres 602 remaining within the delivery catheter lumen are not dislodged. After embolization, an arteriogram can be performed to confirm the completion of the procedure. Arterial flow may still be present to some extent to healthy body tissue proximal to the embolization, while flow to the diseased or targeted tissue is blocked. As a result of the restricted blood flow, the diseased or targeted tissue may begin to shrink.

Study of Resorbable Microspheres in a Swine Model:

A study was conducted in a swine model to evaluate the safety of the present resorbable microspheres including cross-linked gelatin (test article) and to assess the duration of occlusion and occurrence of recanalization compared to the commercially-available, non-resorbable Embosphere® microspheres (Merit Medical Systems Inc., South Jordan, Utah) (control article).

Methods—Animals and Experimental Design:

Embolization was performed in 12 Yucatan miniature swine (60-100 kg), approximately 2 to 3 years of age. Both the test article and the control article were implanted in a branch of the caudal pole artery of the right and left kidney. The 100-300 µm microsphere size was implanted in the right kidney while the 700-1,000 µm microsphere size (700-900 µm for the control article) was implanted in the left kidney. Three animals were survived to each of four time points: 2, 4, 9 and 12 weeks. Animals were randomized to the test article and control groups at a ratio of 2:1 for each time point.

The test article was deployed in the target artery until embolization was achieved, defined as any of the following: (1) appearance of new collateral-reflux flow that was not seen on the initial arteriogram; (2) increased resistance in the target arteries manifested by reflux back along the angiographic catheter; (3) a "pruned-tree" appearance, wherein contrast was no longer observed flowing through smaller arterial branches; or (4) sluggish forward flow in the main target artery with contrast still visible for at least five cardiac beats.

Angiography was performed for each animal prior to the embolization procedure (baseline), after the embolization procedure, and prior to being euthanized. Embolization was confirmed by angiographic demonstration of target artery occlusion at the time of implant. A total of 16 test article and 8 control article implant sites were successfully embolized.

Methods—Safety Assessment:

Tissue implant responses were assessed through gross pathology and histological evaluation of the local test article implant sites at each appointed interval by a board certified veterinary pathologist. Potential local and systemic toxic effects related to the test articles were evaluated through clinical observations, examination of major organs/tissues during gross necropsy by a qualified pathologist, and a comparison of various hematology and coagulation parameters, drawn prior to implant, prior to euthanasia, and at available interims (2, 4 and 9 weeks) for each animal. In addition to tissue response, histology images were used to assess degradation of the test articles and potential recanalization.

Results—Safety:

All animals remained healthy throughout the study, experiencing normal activity and weight gain. There were no adverse events related to the implantation of either the test article or the control article. No clinically significant abnormalities were identified in the pre-surgical, interim or terminal reporting of complete blood count (CBC), differential, or serum chemistry results that appeared to negatively reflect upon either the test articles or control articles. No evidence of systemic toxic effects was observed by examination of major organs/tissues during gross necropsy. As expected, there were infarcts in the kidneys of varying size and shape that were consistent with the vasculature targeted for embolization.

Results—Angiographic Occlusion at Term:

Angiographic images were obtained immediately prior to euthanizing each animal. The images were assessed for embolization of the target vessel. Results were comparable between the test article and the control article. Occlusion was observed at 7/8 sites embolized with 100-300 µm test articles compared to 3/3 sites (one site excluded as baseline images were inadvertently not recorded) embolized with the 100-300 µm control articles. Occlusion was observed at 4/8 sites embolized with 700-1,000 µm test articles compared to 2/4 sites embolized with 700-900 µm control articles.

In several cases, it was noted during implantation that the vasculature in the left kidney (where the larger spheres were implanted) was slightly smaller than that noted in the right kidney. Additionally, upon entering the left kidney vasculature, vascular spasm was noted in some cases. It is possible that these vascular spasms limited the amount of embolic material implanted within the left kidneys.

Results—Histopathology and Occurrence of Recanalization:

All test articles observed histologically were found in the targeted portion of each kidney at each appointed interval. The test articles did not appear to migrate from the intended implant sites. The tissue response to the implanted test articles had a consistent appearance for both sizes of test articles throughout the study. There was both a connective tissue response and an inflammatory response to the spheres. When the test articles were observed within an arterial lumen, fibro-proliferative connective tissue filled the spaces between the articles. Some of this connective tissue was interpreted as being organized thrombus material. As this connective tissue and/or thrombus material formed around the test articles, it is reasonable to assume that the test article material is "anchored" into the target location, even in the presence of material degradation.

No systemic inflammation resulting from test articles was observed. The inflammatory response directed toward the articles was composed of macrophages and multinucleated giant cells arranged immediately adjacent to the articles, consistent with the expected foreign body immune reaction.

Degradation of test articles was mediated by macrophages and multinucleated giant cells, which encircled individual spheres and phagocytized them from the periphery. There were small foci of macrophages and multinucleated giant cells without associated test article material in areas consistent with implant sites. It was presumed that these were sites of complete test article degradation. The test article degradation process appeared to be similar for differing article sizes and at differing intervals post-implantation, although the degradation rate did not appear to be consistent between individual articles. Intact test articles intermingled with degrading articles or foci of presumed degraded articles at all appointed intervals from 4 weeks post-implantation and beyond. Occurrences of test article degradation did not necessarily seem to be accompanied by recanalization.

CONCLUSION

The safety profile of the present test articles was found to be comparable to that of the control articles. No adverse events occurred in either of the investigational groups throughout the course of the study, and no systemic toxic effects were noted during gross necropsy of major tissue/organs.

The test articles were intact, exhibiting no degradation at 2 week post-implantation. Degradation of the test articles was observed starting at 4 weeks. The majority of articles were degraded by 9 weeks, with a few articles still observed histologically at 12 weeks. Vessel occlusion rates, as evaluated by angiography, were found to be similar between the test articles and the control articles at all appointed intervals. Histologic examination showed that the frequency of recanalization was similar between the test articles and the control articles.

The results of this study demonstrated that the test article safety profile, duration of occlusion, and occurrence of recanalization were comparable to a commercially-available non-resorbable microsphere in this swine implant model. Also, the test articles were easy to use, effective for all processes, and the tissue effects of occlusion are controllable.

Figure 8:
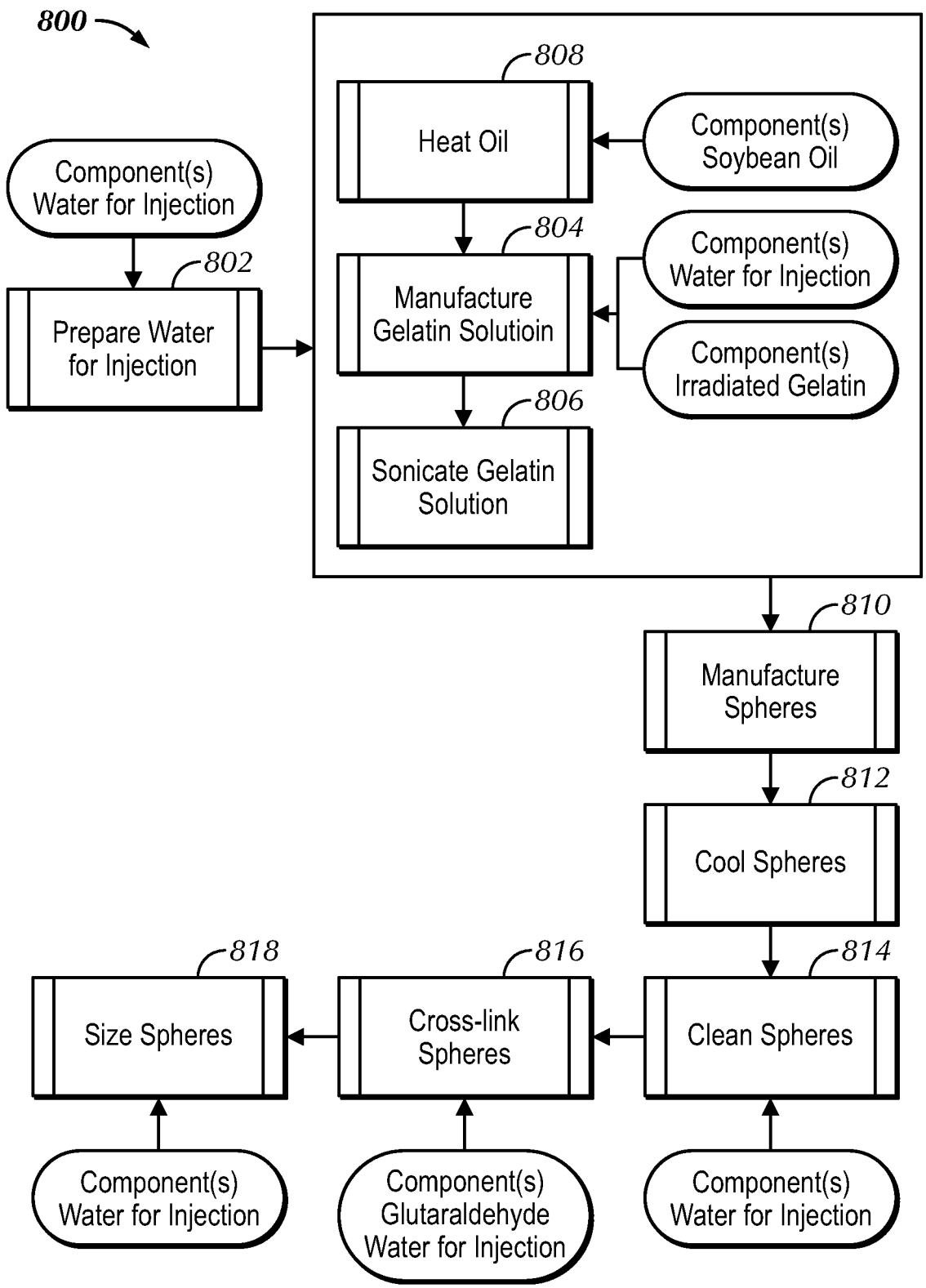
FIG. 8 illustrates a method of manufacturing resorbable microspheres including cross-linked gelatin, as constructed in accordance with at least one embodiment.

Processes for Producing Resorbable Microspheres:

FIG. 8 illustrates a method 800 for manufacturing resorbable microspheres including cross-linked gelatin, as constructed in accordance with at least one embodiment.

An initial step for the preparation of the resorbable microspheres can include the preparation of a gelatin solution, which includes at least 12% irradiated gelatin, such as between about 12% and about 22% of gelatin. In operation 802, about 1900-2100 grams (g) of water (and more preferably about 1995-2005 g of water) can be heated to about 60-70° Celsius (C). In operation 804, about 500-550 g of irradiated gelatin (and more preferably about 515-525 g of irradiated gelatin) can be added to the heated water to form the gelatin solution. The gelatin and water can be allowed to mix for a period of time, such as up to about 90 minutes (mins), at a propeller speed of about 200-400 revolutions per minutes (RPM). Optionally, a marker or an active agent can be added to the gelatin solution. In operation 806, the gelatin solution can be sonicated to remove air. In one embodiment, a sonicator can receive the gelatin solution and be powered on for 15-30 mins at a power of 50-70% and a temperature of 40-55° C.

After the gelatin solution is free or substantially free of air, microspheres can be created. In operation 808, about 20-30 kg of soybean, mineral or other equivalent oil (and more preferably 26-28 kg of oil) can poured into a tank and heated to a temperature between about 30-40° C. (and more preferably 36-38° C.). In operation 810, the sonicated gelatin solution can be introduced into a pressure vessel and allowed to cool to a temperature of about 42-44° C. The lid on the pressure vessel can be secured and the gelatin solution can be introduced into the heated oil at a pressure of about 3-4 pounds per square inch (PSI), if microspheres having a diameter of 100-500 μm are desired, or about 8-10 PSI, if microspheres having a diameter of about 500-1,000 μm are desired. The mixture of gelatin solution and oil can be stirred at a propeller speed of about 480-510 RPM, if microspheres having a diameter of 100-300 μm are desired, about 240-260 RPM, if microspheres having a diameter of 300-500 μm are desired, or about 195-215 RPM, if microspheres having a diameter of 500-1,000 μm are desired.

With microspheres of a desired size created, they can be cooled and cleaned prior to be cross-linked. In operation 812, the microspheres can be transferred to a chiller to be cooled to a temperature between about 1-12° C. (and more preferably 2-6° C.). In operation 814, the cooled microspheres can be cleaned by placing them in a centrifuge and setting the centrifuge to a temperature of about 2-6° C. The oil can initially be gently decanted off for each collection of microspheres. The microspheres can be further clean by centrifuge. In one embodiment, the centrifuge process takes about 4-6 mins at a speed of about 950-1050 RPM. Finally, the microspheres can be washed using a heat exchanger or pressurized tank. The water used to wash the microspheres can have a temperature less than or equal to about 18° C., a flow rate of about 1.2-1.8 gallons per minute (GPM), and/or a pressure of about 4 PSI or less.

The cleaned microspheres can be cross-linked at about room temperature (15-25° C.), in operation 816, using water and glutaraldehyde. About 9.15-9.25 kg of water and 750-850 mL of 25% glutaraldehyde can be added to a carboy. This can create about a 2-4% glutaraldehyde solution. The carboy can be sealed and shaken using an orbital shaker operating at 80-90 RPM for about 2-3 mins. The microspheres can then be transferred into the carboy, with the carboy resealed for further shaking after the transfer. The carboy, including the glutaraldehyde solution and the microspheres, can be allowed to shake and cross-link for about 25-35 mins.

Finally, in operation 818, the microspheres can be separated by size category, washed to eliminate any trace of secondary product, and sterilized. Standard sieves having sizes of 125 μm, 212 μm, 355 μm, 425 μm, 560 μm, 630 μm, 800 μm, and 900 μm, for example, can be used to associate each microsphere into a particle size of 100-300 μm, 300-500 μm, 500-700 μm, or 700-1,000 μm, for example. Water at a pressure of about 1.5-1.7 GPM can be used to rinse the categorized microspheres. Sterilization of the microspheres can include reducing the temperature of the microspheres to about 8° C. or less and/or irradiated using e-beam or gamma.

The method 800 for manufacturing resorbable microspheres can optionally include additional steps or operations. For example, the microspheres can be packaged in syringes along with a liquid carrier for distribution to physicians. Alternatively, the microspheres can be vacuum-dried and placed into vials for distribution to physicians.

CLOSING NOTES AND EXAMPLES

Embolization of a lumen can be useful for a variety of medical reasons, including preventing or controlling bleeding due to lesions or to ablate diseased tissue by cutting off blood supply. Embolization can be used before surgery, such as to shrink tumor size or aid in visualization, or during or immediately following surgery to prevent blood loss.

The present embolic materials, suspensions, kits and methods include or use resorbable microspheres having cross-linked gelatin as their primary ingredient. The spherical shape and calibrated size ranges of the microspheres offer smooth delivery and predictable distribution within a lumen. In addition, spherical particles can penetrate to a target region within vasculature more easily than traditional irregularly-shaped particles due to their uniform shape. The resorbable nature of the microspheres allows for the temporary blockage of blood flow to a punctured or diseased site, which can be beneficial in numerous clinical situations, for example, trauma, postpartum hemorrhage and GI bleeding.

The above Detailed Description includes references to the accompanying drawings, which form a part of the Detailed Description. The Detailed Description should be read with reference to the drawings. The drawings show, by way of illustration, specific embodiments in which the present embolic materials, suspensions, kits and methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, an embolic material can comprise a resorbable microsphere including cross-linked gelatin as its primary ingredient and having a substantially spherical shape with a diameter of about 50 μm to about 1,500 μm.

In Example 2, the embolic material of Example 1 can optionally further comprise a marker.

In Example 3, the embolic material of Example 2 can optionally be configured such that the marker is selected from the group consisting of a dye, an imaging agent, and a contrast agent.

In Example 4, the embolic material of any one or any combination of Examples 1-3 can optionally further comprise an active agent.

In Example 5, the embolic material of Example 4 can optionally be configured such that the active agent includes a chemotherapy agent or anti-angiogenic agent.

In Example 6, the embolic material of any one or any combination of Examples 1-5 can optionally be configured such that the gelatin is cross-linked with glutaraldehyde or formaldehyde.

In Example 7, the embolic material of any one or any combination of Examples 1-6 can optionally be configured such that the microsphere resorbs during an in vivo time period of between 24 hours and 2 weeks, inclusive.

In Example 8, the embolic material of any one or any combination of Examples 1-6 can optionally be configured such that the microsphere resorbs during an in vivo time period of between about 3 weeks and about 15 weeks, inclusive.

In Example 9, the embolic material of any one or any combination of Examples 1-8 can optionally be configured such that the gelatin is purified porcine skin gelatin.

In Example 10, the embolic material of any one or any combination of Examples 1-9 can optionally be configured such that the microsphere is compressible.

In Example 11, an injectable embolization suspension disposed in a pre-loaded application can comprise a plurality of resorbable microspheres, as recited in any one or any combination of Examples 1-10, and a liquid carrier.

In Example 12, the embolization suspension of Example 11 can optionally be configured such that the liquid carrier includes saline.

In Example 13, the embolization suspension of any one of Examples 11 or 12 can optionally be configured such that the liquid carrier includes a contrast agent.

In Example 14, the embolization suspension of any one or any combination of Examples 11-13 can optionally be configured such that the plurality of resorbable microspheres has a diameter between about 100 micrometers and about 300 micrometers, inclusive.

In Example 15, the embolization suspension of any one or any combination of Examples 11-13 can optionally be configured such that the plurality of resorbable microspheres has a diameter between about 300 micrometers and about 500 micrometers, inclusive.

In Example 16, the embolization suspension of any one or any combination of Examples 11-13 can optionally be configured such that the plurality of resorbable microspheres has a diameter between about 500 micrometers and about 700 micrometers, inclusive.

In Example 17, the embolization suspension of any one or any combination of Examples 11-13 can optionally be configured such that the plurality of resorbable microspheres has a diameter between about 700 micrometers and about 1,000 micrometers, inclusive.

In Example 18, a method of forming an embolic material can comprise preparing a gelatin solution by combining water and at least 12% irradiated gelatin; sonicating the gelatin solution to remove air; introducing the gelatin solution into heated oil to form a mixture of gelatin solution and oil; agitating the mixture to form a plurality of resorbable microspheres having a substantially spherical shape with a diameter ranging from about 50 micrometers to about 1,500 micrometers, inclusive; and cross-linking the plurality of resorbable microspheres.

In Example 19, the method of Example 18 can optionally be configured such that preparing the gelatin solution includes combining a marker material to the water and the gelatin.

In Example 20, the method of any one of Examples 18 or 19 can optionally be configured such that introducing the gelatin solution into heated oil includes introducing the gelatin solution into heated soybean oil or heated mineral oil.

In Example 21, the method of any one or any combination of Examples 18-20 can optionally further comprise cleaning the plurality of resorbable microspheres.

In Example 22, the method of any one or any combination of Examples 18-21 can optionally be configured such that cleaning the plurality of resorbable microspheres includes placing the microspheres in a centrifuge.

In Example 23, the method of any one or any combination of Examples 18-22 can optionally be configured such that cross-linking the plurality of resorbable microspheres includes agitating the microspheres with glutaraldehyde.

In Example 24, the method of any one or any combination of Examples 18-23 can optionally further comprise separating the plurality of resorbable microspheres using sieves to obtain calibrated size ranges of microspheres.

In Example 25, the method of any one or any combination of Examples 18-24 can optionally further comprise sterilizing the plurality of resorbable microspheres by reducing a temperature of the microspheres to about 8 degrees Celsius or less.

In Example 26, the method of any one or any combination of Examples 18-25 can optionally further comprise vacuum-drying the microspheres and placing them into a vial.

In Example 27, the method of any one or any combination of Examples 18-26 can optionally be configured such that sizes of the plurality of resorbable microspheres are based, at least in part, on a temperature of the gelatin solution when prepared, a temperature of the heated oil when the gelatin solution is introduced, the rate of introduction of the gelatin solution into the heated oil, and the rate of agitation of the mixture including gelatin solution and heated oil.

The scope of the present embolic materials, suspensions, kits and methods should be determined with reference to the appended claims, along with the full scope of equivalents to which such claims are entitled. In the appended claims, the terms "including" and "in which" are used as the plain-English equivalents of the respective terms "comprising" and "wherein." Also in the following claims, the terms "including" and "comprising" are open-ended; that is, a material, kit or method that includes features or components in addition to those listed after such a term in a claim are still deemed to fall within the scope of that claim. Moreover, the terms "first," "second" and "third," etc. in the following claims are used merely as labels, and such terms not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An embolic material, comprising:
resorbable microspheres formed from a sonicated solution of gelatin and water, wherein the sonicated solution comprises between at least 12% and up to 22% gelatin, wherein the microspheres are each free of air and have a substantially spherical shape reinforced by cross-linking the gelatin with glutaraldehyde or formaldehyde,
wherein the microspheres each include a radioactive agent, and
wherein the microspheres are unconnected and resistant to aggregation.

2. The embolic material of claim 1, wherein each of the microspheres includes a marker.

3. The embolic material of claim 1, wherein each of the microspheres is compressible.

4. The embolic material of claim 3, wherein each of the microspheres resorbs during an in vivo time period of between about 24 hours and 15 weeks, inclusive.

5. The embolic material of claim 1, wherein the radioactive agent comprises strontium, rhenium, yttrium, technetium, cobalt, or a combination thereof.

6. The embolic material of claim 1, wherein each of the microspheres further comprises a prophylactic agent, a therapeutic agent, a diagnostic agent, or a combination thereof.

7. An embolic material, comprising:
 resorbable microspheres formed from a sonicated solution of water and gelatin,
 wherein the sonicated solution comprises between at least 12% and up to 22% gelatin,
 wherein the microspheres are each free of air and have a substantially spherical shape reinforced by cross-linking the gelatin with glutaraldehyde or formaldehyde, and
 wherein the microspheres are unconnected and resistant to aggregation.

8. The embolic material of claim 7, wherein each of the microspheres further includes a marker.

9. The embolic material of claim 7, wherein each of the microspheres further includes a radioactive agent comprising strontium, rhenium, yttrium, technetium, cobalt, or a combination thereof.

10. The embolic material of claim 7, wherein each of the microspheres further includes a prophylactic agent, a therapeutic agent, a diagnostic agent, or a combination thereof.

11. A kit comprising:
 an effective amount of an injectable embolization suspension disposed in a pre-loaded applicator;
 wherein the suspension includes a liquid carrier and the resorbable microspheres of claim 1; and
 wherein the microspheres are suitable for embolization.

12. The kit of claim 11, further comprising a delivery catheter that can be placed into a lumen.

13. The kit of claim 11, wherein each of the microspheres includes a marker.

14. The kit of claim 11, wherein the radioactive agent comprises strontium, rhenium, yttrium, technetium, cobalt, or a combination thereof.

* * * * *